(12) United States Patent
Thompson et al.

(10) Patent No.: US 10,466,147 B2
(45) Date of Patent: Nov. 5, 2019

(54) METHODS AND APPARATUSES FOR DETECTING MICROSCOPE SLIDE COVERSLIPS

(71) Applicant: Ventana Medical Systems, Inc., Tucson, AZ (US)

(72) Inventors: Michael J. Thompson, Tucson, AZ (US); Charles Nathan Hassen, Tucson, AZ (US)

(73) Assignee: Ventana Medical Systems, Inc., Tucson, AZ (US)

(*) Notice: Subject to any disclaimer, the term of this patent is extended or adjusted under 35 U.S.C. 154(b) by 0 days.

(21) Appl. No.: 16/043,110

(22) Filed: Jul. 23, 2018

(65) Prior Publication Data
US 2019/0041301 A1 Feb. 7, 2019

Related U.S. Application Data

(63) Continuation of application No. 13/786,356, filed on Mar. 5, 2013, now Pat. No. 10,156,503.

(51) Int. Cl.
| | |
|---|---|
| *G01N 1/31* | (2006.01) |
| *G02B 21/34* | (2006.01) |
| *G02B 1/11* | (2015.01) |
| *B65H 7/14* | (2006.01) |
| *G01N 35/00* | (2006.01) |
| *G01J 1/02* | (2006.01) |
| *G01J 1/00* | (2006.01) |

(52) U.S. Cl.
CPC ............ *G01N 1/312* (2013.01); *G01J 1/0238* (2013.01); *G01N 35/00029* (2013.01); *G02B 1/11* (2013.01); *G02B 21/34* (2013.01); *B65H 7/14* (2013.01); *G01N 2035/00079* (2013.01)

(58) Field of Classification Search
None
See application file for complete search history.

(56) References Cited

U.S. PATENT DOCUMENTS

| | | | |
|---|---|---|---|
| 4,922,112 A | 5/1990 | Zierl et al. | |
| 5,566,249 A | 10/1996 | Rosenlof et al. | |
| 5,625,706 A | 4/1997 | Lee et al. | |
| 5,638,459 A * | 6/1997 | Rosenlof ............ | G06K 9/00127 |
| | | | 382/133 |
| 5,812,692 A | 9/1998 | Rosenlof et al. | |
| 6,544,798 B1 | 4/2003 | Christensen et al. | |
| 6,759,011 B1 | 7/2004 | Richards et al. | |
| 6,855,559 B1 | 2/2005 | Christensen et al. | |
| 7,303,725 B2 | 12/2007 | Reinhardt et al. | |
| 8,213,001 B2 | 7/2012 | Tomisek et al. | |

(Continued)

FOREIGN PATENT DOCUMENTS

WO 2008/046593 4/2008

*Primary Examiner* — Neil N Turk
(74) *Attorney, Agent, or Firm* — Perkins Coie LLP (57) ABSTRACT

A system is capable of detecting substrates and can differentiate between zero, one, or multiple transparent or semi-transparent substrates in a stack. The system can include an optical sensor, an optically anti-reflective element, and a detector. The optical sensor outputs light towards the optically anti-reflective element. The light detector is positioned to detect light from the light source that is reflected by substrates, if any, positioned within a detection zone between the optically anti-reflective element and the detector.

26 Claims, 9 Drawing Sheets

(56) References Cited

U.S. PATENT DOCUMENTS

| | | |
|---|---|---|
| 2005/0156046 A1 | 7/2005 | Goldenberg |
| 2009/0129660 A1 | 5/2009 | Gregson |
| 2010/0165326 A1* | 7/2010 | Tomisek .................. B65H 7/12 356/51 |

* cited by examiner

METHODS AND APPARATUSES FOR DETECTING MICROSCOPE SLIDE COVERSLIPS

CROSS REFERENCE TO RELATED APPLICATION

This application is a continuation of U.S. application Ser. No. 13/786,356, filed on Mar. 5, 2013 (U.S. Pat. No. 10,156,503), which is hereby incorporated by reference in its entirety.

TECHNICAL FIELD

This disclosure relates to methods and apparatuses for processing microscope slides and analyzing substrates. In particular, the disclosure relates to methods and apparatuses for detecting slides, coverslips for microscope slides, and processing specimens on microscope slides.

BACKGROUND

A wide variety of techniques have been developed to prepare and analyze biological samples for analysis. Biological samples, e.g., tissue sections or cells, can be mounted on microscope slides for diagnostic purposes. The biological samples are often treated with one or more substances (e.g., dyes, reagents, etc.) to add color and contrast to otherwise transparent or invisible cells or cell components. The treated biological samples are often covered with coverslips to avoid contamination of the biological samples and to permit long-term archiving of the slides.

Automated coverslippers can be used to automatically place glass coverslips on specimen-bearing microscope sides. For example, automated coverslippers often pick up a coverslip from a stack of coverslips and place the coverslip onto a specimen-bearing slide. Unfortunately, automated coverslippers can pick up more than one coverslip because coverslips frequently stick together due to static forces, vander waal forces, or moisture between adjacent coverslips. This may result in two or more coverslips being mounted on a slide. It may be difficult to remove the excess coverslip(s) from the slide. If the automated coverslipper attempts to transport stuck-together slides, coverslips may drop resulting in loose coverslips in automated processing equipment. The loose coverslips can result in damage and/or malfunction of the automated processing equipment and may result in "downtime" for maintenance. Unfortunately, automated coverslippers are not capable of accurately counting coverslips during handling.

Overview of Technology

At least some embodiments of the technology are directed to a system for detecting substrates. The system is capable of differentiating between zero, one, or multiple substrates in a stack. The system can detect substrates in the form of, for example, coverslips (e.g., coverslips for microscope slides), screens (e.g., transparent screens for computing devices, smartphones, tablets, or the like), protective sheets, or other items through which electromagnetic radiation is capable of traveling. The substrates can be transparent or semi-transparent.

In some embodiments, a system for detecting substrates includes an optically anti-reflective element and an optical sensor. The optical sensor includes a light source and a light detector. The light source is positioned to output light towards the optically anti-reflective element. The light detector is positioned to detect the light reflected by one or more substrates located between the light detector and the optically anti-reflective element. Information about the substrates can be determined based on the reflected light. The information can include, for example, the presence of substrates, the number of substrates, optical properties of the substrates, or the like. For example, the reflected light can be used to count the number of substrates in a stack of substrates.

The optically anti-reflective element, in some embodiments, can absorb incident or impinging light to manage noise (e.g., optical noise). The noise can be, for example, light reflected from surfaces adjacent to the substrates. In some embodiments, the optically anti-reflective element can be positioned to limit, reduce, or substantially eliminate noise caused by such reflected light. The reflected light (i.e., the signal from the substrates) received by the light detector can thus be used to accurately detect the substrates.

In some embodiments, a substrate analyzer can include an optical sensor and an optical element. A holder mechanism can carry one or more substrates to a detection zone between the sensor and optical element. The substrate analyzer can evaluate the detection zone to count the number of substrates, if any, within the detection zone. The optical sensor can be carried by, or part of, the holder mechanism such that the optical sensor is properly positioned with respect to the substrate. In some embodiments, the optical sensor and optical element are stationary. The holder mechanism can carry substrates into the detection zone. In other embodiments, the optical sensor can be stationary and the optical element is part of the holder mechanism.

In some embodiments, a detector comprises an optical element and an optical sensor. In one embodiment, the optical element is a noise-reducing element that inhibits, limits, or substantially prevents the reflection of light that has traveled through a stack of substrates. The noise-reducing element can include, without limitation, one or more optically anti-reflective elements with low-remission surfaces, light-absorbing characteristics, or the like.

In some embodiments, a slide processing apparatus includes a processing station configured to process a specimen on a microscope slide and a coverslipper. The coverslipper receives and applies coverslips to microscope slides processed by the processing station. The coverslipper can include one or more coverslip detectors used to detect coverslips. A coverslip detector, in some embodiments, includes an optically anti-reflective element and an optical sensor. The optical sensor is positioned to deliver light along a path towards the anti-reflective element and to detect light reflected by any coverslips positioned along the path. In some embodiments, the coverslip detectors can include an array of light sensors and detectors to simultaneously analyze multiple coverslips.

In one embodiment, a detection method comprises delivering light towards a coverslip such that a portion of the light is reflected by the coverslip and a portion of the light travels through the coverslip and strikes an optically anti-reflective element. The light reflected by the coverslip can be detected to, for example, determine a presence or a number of coverslips. In one embodiment, the coverslip is held against the optically anti-reflective element while detecting the reflected light. For example, the coverslip can cover the optically anti-reflective element.

In some embodiments, a method of detecting substrates includes carrying at least one substrate to a detection zone using a holder mechanism. The detection zone can be located between a light detector and an optically anti-reflective element. Light is delivered towards the optically anti-reflective element such that a portion of the light is reflected by the substrate and a portion of the light, which travels through the substrate, strikes the optically anti-reflective element. The light reflected by the substrate can be detected, and a number of substrates at the detection zone can be determined based on the detected light.

A delivery location of the substrates can be determined based, at least in part, on the presence or number of substrates. A controller, in some embodiments, can determine the delivery location based on the number of detected substrates. In some embodiments, the controller can command the holder mechanism to move the substrates to a first location if one substrate is detected and a second location a plurality of substrates are detected.

BRIEF DESCRIPTION OF THE DRAWINGS

Non-limiting and non-exhaustive embodiments are described with reference to the following drawings. The same reference numerals refer to like parts or acts throughout the various views, unless otherwise specified.

DETAILED DESCRIPTION OF TECHNOLOGY

Figure 1:
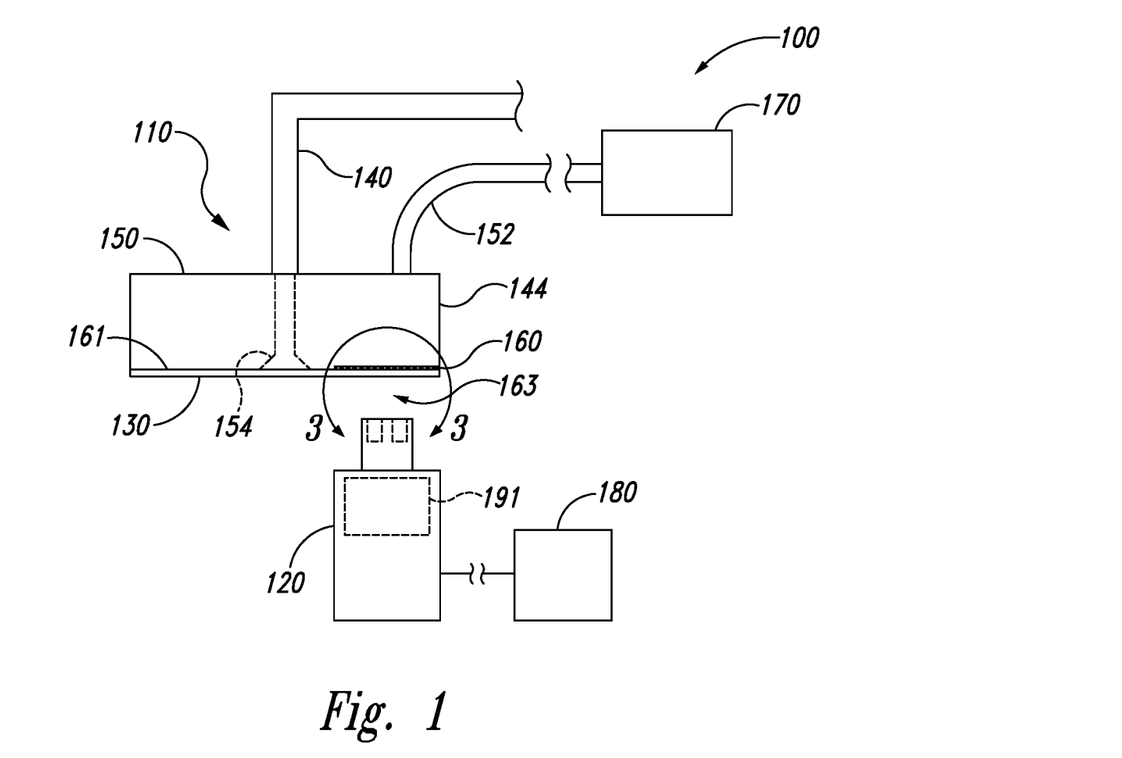
FIG. 1 is a front view of a coverslip detector in accordance with one embodiment.
Figure 2:
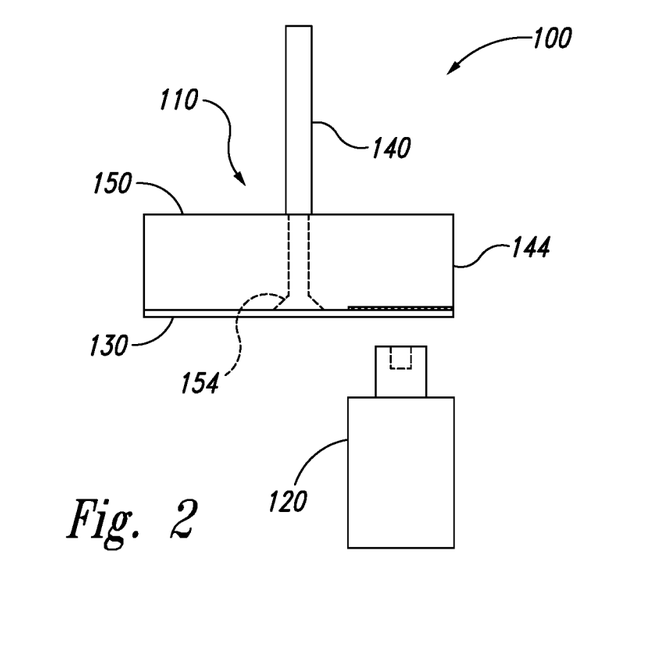
FIG. 2 is a side view of the coverslip detector of FIG. 1.

FIGS. 1 and 2 are front and side views of a coverslip detector 100 in accordance with one embodiment. The coverslip detector 100 can include a coverslip transport apparatus 110 ("transport apparatus 110") for carrying microscope slide coverslips and an optical sensor 120 for detecting coverslips. The transport apparatus 110 is shown carrying a single microscope slide coverslip 130. A detection enhancing element in the form of an optically anti-reflective element 160 ("anti-reflective element 160") can be positioned behind the surface of the coverslip 130 opposite the optical sensor 120. The anti-reflective element 160 can enhance performance of the optical sensor 120 to accurately detect a presence and/or number of coverslips held by the transport apparatus 110. The enhanced performance can include, without limitation, increasing the detection range of the sensor 120, reducing or limiting noise to increase a signal-to-noise ratio, managing scattering of light, or combinations thereof. After the optical sensor 120 determines that the transport apparatus 110 is carrying the single coverslip 130, the coverslip 130 can be placed on a specimen-bearing microscope slide. If the optical sensor 120 detects multiple coverslips, the transport apparatus 110 can transport the coverslips to a coverslip collection station or another desired location. If the optical sensor 120 determines that the transport apparatus 110 is unloaded, the transport apparatus 110 can obtain a coverslip.

The optical sensor 120 can be a photoelectric proximity sensor configured to output light towards the anti-reflective element 160 and detect light reflected by the coverslip 130. In some embodiments, the detection of light can include, for example, one or more of determining the presence of light, measuring light intensity, comparing measured light intensity to a reference light intensity, or the like. The anti-reflective element 160 can minimize, limit, or substantially eliminate reflection of light that has traveled through the coverslip 130 because such reflected light may result in noise. The percentage of incident light from the sensor 120 absorbed or otherwise captured by the anti-reflective element 160 can be increased or decreased to increase or decrease the signal (e.g., light intensity associated with light reflected by the coverslips) to noise ratio.

Referring to FIG. 1, the transport apparatus 110 can include a transport mechanism 140 and a coverslip holder mechanism 144 ("holder mechanism 144"). The transport mechanism 140 can move the holder mechanism 144 to position at least a portion of the coverslip 130 within a coverslip detection zone 163. The transport mechanism 140 can include, without limitation, one or more robotic arms, conveyors, motors (e.g., stopper motors, drive motors, etc.), rail assemblies (e.g., carriage and linear rail assemblies), controllers, combinations thereof, or the like. The components and configuration of the transport mechanism 140 can be selected based on the desired movement of the holder mechanism 144.

The holder mechanism 144 can include a main body 150, a fluid line 152, and a pickup head 154 ("head 154"). The head 154 is positioned in the main body 150 and is shown in dashed line. The main body 150 can have a one-piece construction or a multi-piece construction and can fluidically couple the fluid line 152 to the head 154. The line 152 can include, without limitation, one or more conduits (e.g., hoses), valves, or other fluid components for establishing a fluidic connection between the main body 150 and a pressurization device 170. The head 154 can be a suction head (e.g., a suction cup) capable of maintaining a vacuum with the coverslip 130. The pressurization device 170 can draw a vacuum such that a sufficient vacuum is maintained to securely hold the coverslip 130. To release the coverslip 130, the vacuum can be reduced or eliminated. The pressurization device 170 can include, without limitation, one or more vacuum devices, pumps, or the like.

A controller 180 can be in communication with the sensor 120 and can determine the number of coverslips carried by the holder mechanism 144. In some embodiments, the controller 180 can correlate the detected light to the absence, presence, and/or number of coverslips based on signals from the sensor 120. The controller 180 can thus determine the number of coverslips based on the total amount of detected light because the total amount of received light can be directly related to the number of coverslips. The controller 180 can also be integrated into the sensor 120.

Figure 3:
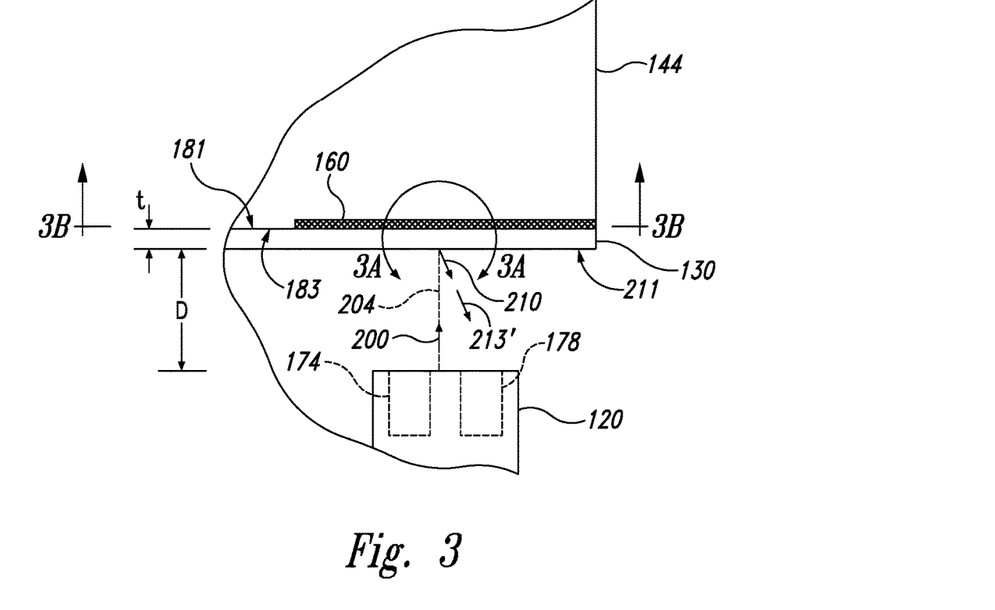
FIG. 3 is a detailed view of the coverslip detector of FIG. 1.

FIG. 3 is a detailed view of the coverslip 130 held flat against the holder mechanism 144. A back surface 181 of the coverslip 130 can be held in contact with a contact surface 183 of the holder mechanism 144 to minimize scattering of light transmitted through the coverslip 130 and/or to prevent unwanted movement of the coverslip 130. In other embodiments, the back surface 181 of the coverslip 130 can be spaced apart from the contact surface 183 to prevent or inhibit sticking of the coverslip 130 to the holder mechanism 144.

The sensor 120 can be a proximity sensor. Proximity sensors include, without limitation, photoelectric proximity sensors (e.g., retro-reflective photoelectric proximity sensors, diffuse-reflective photoelectric proximity sensors, etc.) or other sensors capable of detecting coverslips based on, for example, optical analysis (e.g., analysis of reflected light, scattered light, etc.). Advantageously, a distance (i.e., a detector distance) at which the sensor 120 detects a signal above a target threshold can increase for additional coverslips. In some embodiments, the detector distance D can increase, for example, about 60 times the thickness 0.18 mm (0.007 inch) of each additional coverslip. Thus, the detection distance D for two coverslips can be 10.8 mm greater than the detection distance D for a single coverslip. In one embodiment, the sensor 120 is a photoelectric proximity sensor from Sick AG, Waldkirch, DE or similar sensor capable of accurately detecting the presence of the coverslip 130. The sensor 120 can include a positioner mechanism 191 (shown in dashed line in FIG. 1) to move the optical sensor 120 towards or away from the coverslip 130 to adjust the distance D, thereby providing detection flexibility.

Figure 3A:
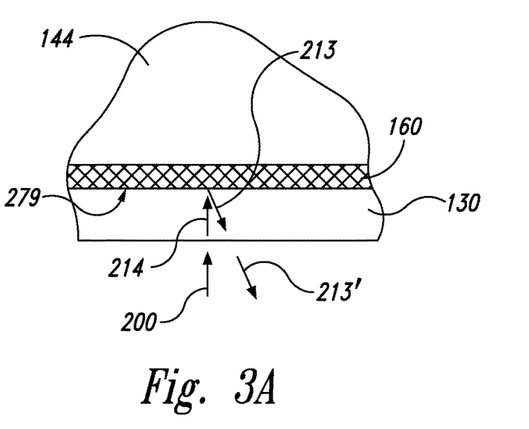
FIG. 3A is a detailed view of an anti-reflective coating and coverslip cross-section.

FIGS. 3 and 3A are detailed views of the coverslip detector 100 and coverslip 130. Referring to FIG. 3, the optical sensor 120 can include a light source 174 and a light detector 178. The light source 174 can emit light 200 (e.g., a beam of light) that travels generally along a light/optical path 204 towards the coverslip 130. A front surface 211 of the coverslip 130 can reflect a portion of the incident light 200. The reflected light (represented by arrow 210) can be received by the light detector 178, and transmitted light (represented by arrow 214 in FIG. 3A) can be absorbed by the anti-reflective element 160. The percentage of transmitted light 214 absorbed by the anti-reflective element 160 can be selected to keep the signal-to-noise ratio at or above a desired level.

In some embodiments, the anti-reflective element 160 may reflect a portion of the light 214. This reflected light (represented by arrow 213 in FIG. 3A) can travel through the coverslip 130 towards the detector 178. There may be transmission losses due to transmission through the coverslip 130. The signal (i.e., the light) detected by the detector 178 can correspond to the sum of the light 210, 213'.

Referring again to FIG. 3, the light source 174 can include, without limitation, one or more light sources or light generators capable of emitting electromagnetic radiation, including, but not limited to, visible light waves, non-visible light waves, infrared light waves, or combinations thereof. The light sources can be, for example, light emitting diodes (e.g., edge emitting LEDs, surface emitting LEDs, super luminescent LEDs), laser diodes, or other suitable light-emitting sources. The light detector 178 can detect radiation wavelength(s) or waveband(s) that corresponds with, or at least overlap with, the wavelength(s) or waveband(s) outputted by the light source 174. The optical sensor 120 can also include, without limitation, one or more optic elements (e.g., lenses, filters, etc.), amplifiers, power supplies, circuitry, memory, controllers, or the like.

The optically anti-reflective element 160 can inhibit, minimize, or substantially prevent the reflection of incident light. In some embodiments, the optically anti-reflective element 160 has reflectivity (or reflectance) of about 0.5 or less for the light outputted by the light source 174. In some embodiments, the light detector 178 includes a photoelectric receiver configured to detect light at one or more wavelengths, and the optically anti-reflective element 160 can have a reflectivity (e.g., a reflectivity equal to or less than about 0.5, 0.25, or 0.1) for the light at the one or more wavelengths. In one embodiment, the optically anti-reflective element 160 has a reflectivity (or reflectance) of about 0.25 or less for the light outputted by the light source 174 or the light detectable by the light detector 178. In one embodiment, the optically anti-reflective element 160 has a reflectivity (or reflectance) of about 0.1 or less for the light outputted by the light source 174 or the light detectable by the light detector 178. The optical characteristics of the anti-reflective element 160 can be selected based on the light emitted by the light source 174 and capabilities of the light detector 178.

In some embodiments, the anti-reflective element 160 is a light-absorbing, low-remission surface. For example, the light-absorbing, low-remission surface can be an anodized surface. The percentage of incident light reflected from the anodized surface (e.g., anodized aluminum) can be less than 50% of the incident light striking the anti-reflective element 160. In one embodiment, the low-remission surface can be a coating, such as a light absorbing coating. In one embodiment, the anti-reflective element 160 is a black coating, black film, black piece of plastic (e.g., a piece of plastic with a black surface), or black paper. In one embodiment, the anti-reflective element 160 includes a light absorbing element and an anti-reflection coating on the light absorbing element. The optical characteristics and configuration of the optically anti-reflective element 160 can be selected to achieve the desired detected signal. Such optical characteristics can include a low reflectivity, low reflection (e.g., low specular reflection, low diffuse reflection, etc.), or the like. The percentage of incident light that is absorbed by the element 160 can be increased or decreased to increase or decrease a ratio of the amount of reflected light 210 to the amount of light 213.

Figure 3B:
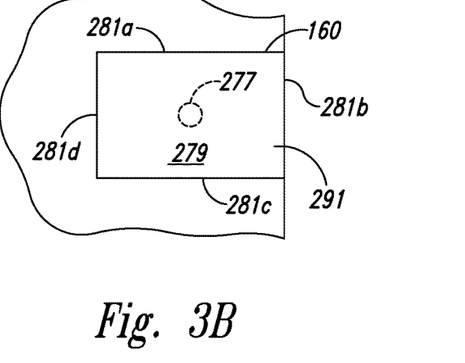
FIG. 3B is a detailed view of an optical element along line-line 3B-3B of FIG. 3.

FIG. 3B is a detailed view of the anti-reflective element 160 along line-line 3B-3B of FIG. 3. A target or exposure area 277 (illustrated in dashed line) is the area that can be illuminated by the sensor 120. The entire area 277 can be located along an exposed surface 279 of the anti-reflective element 160 and can be spaced apart from edges 281a, 281b, 281c, 281d. If the coverslip 130 scatters the transmitted light, a region 291 of the anti-reflective element 160 surrounding the area 277 can absorb the scattered light. In some embodiments, the target area 277 can be positioned at a central region of the anti-reflective element 160.

Figure 4:
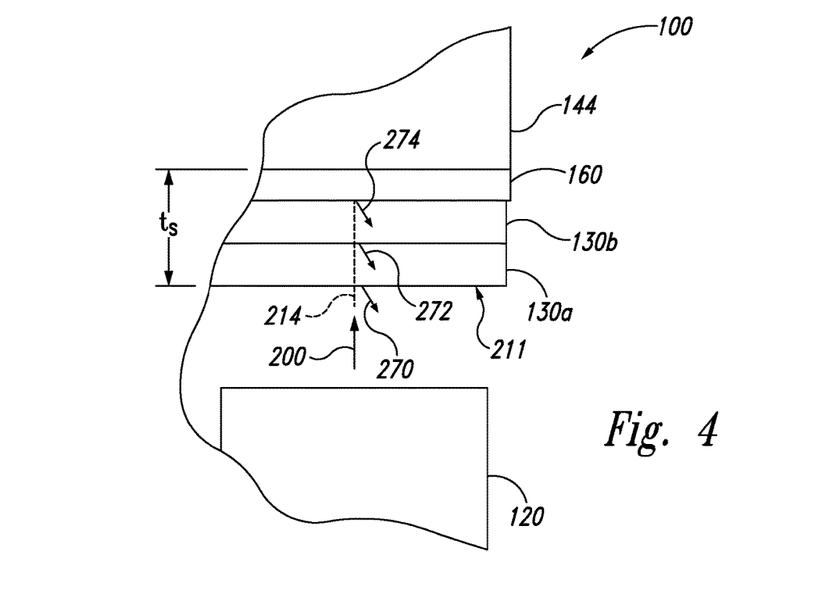
FIG. 4 is a detailed view of a coverslip detector holding two coverslips.

FIG. 4 is a detailed view of the coverslip detector 100 holding two coverslips 130a, 130b (collectively "coverslips 130") along a light path 214. Light (represented by arrow 200) from the optical sensor 120 can be reflected by each of the coverslips 130. The optical sensor 120 can detect light (represented by arrow 270) reflected by the coverslip 130a and light (represented by arrow 272) reflected by the coverslip 130b, as well as light (represented by arrow 274), if any, reflected by the optically anti-reflective element 160. The optical sensor 120 can detect the received light, which comprises the light 270, 272, 274, and output a signal corresponding to the detected light. Because the return signal (i.e., the received light) can increase significantly for each additional coverslip, the return signal can be strongly correlated to the number of coverslips 130 and weakly correlated to the thickness $t_s$ of the stack.

Figure 5:
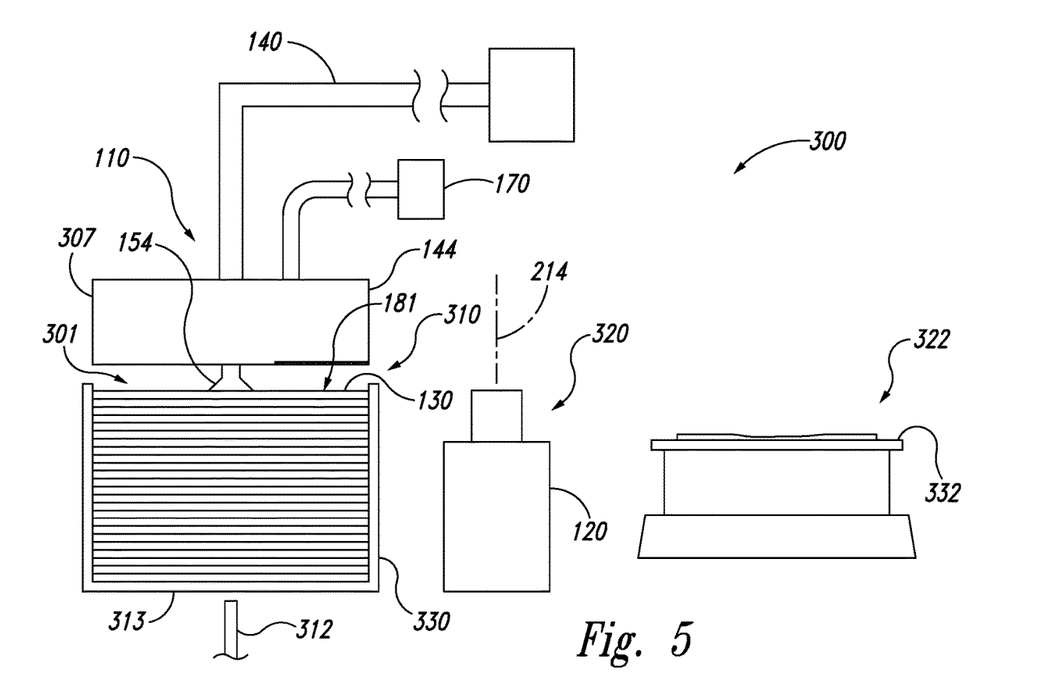
FIG. 5 is a front view of an automated coverslipper ready to pick up a coverslip in accordance with one embodiment.
Figure 6:
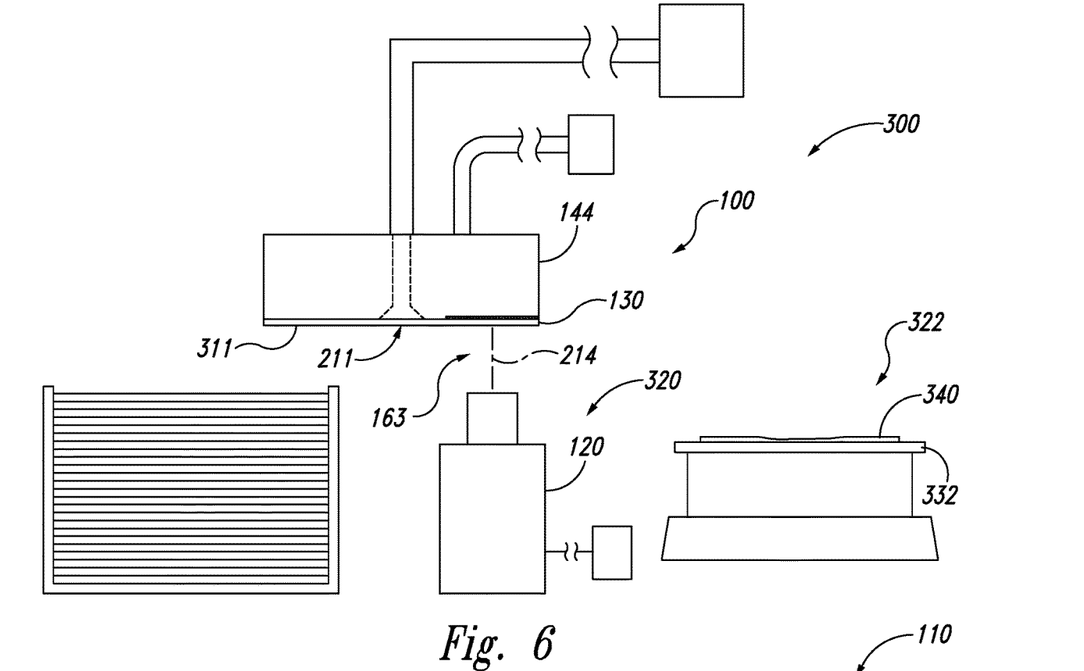
FIG. 6 is a front view of the coverslipper of FIG. 5 holding a coverslip proximate to an optical sensor in accordance with one embodiment.
Figure 7:
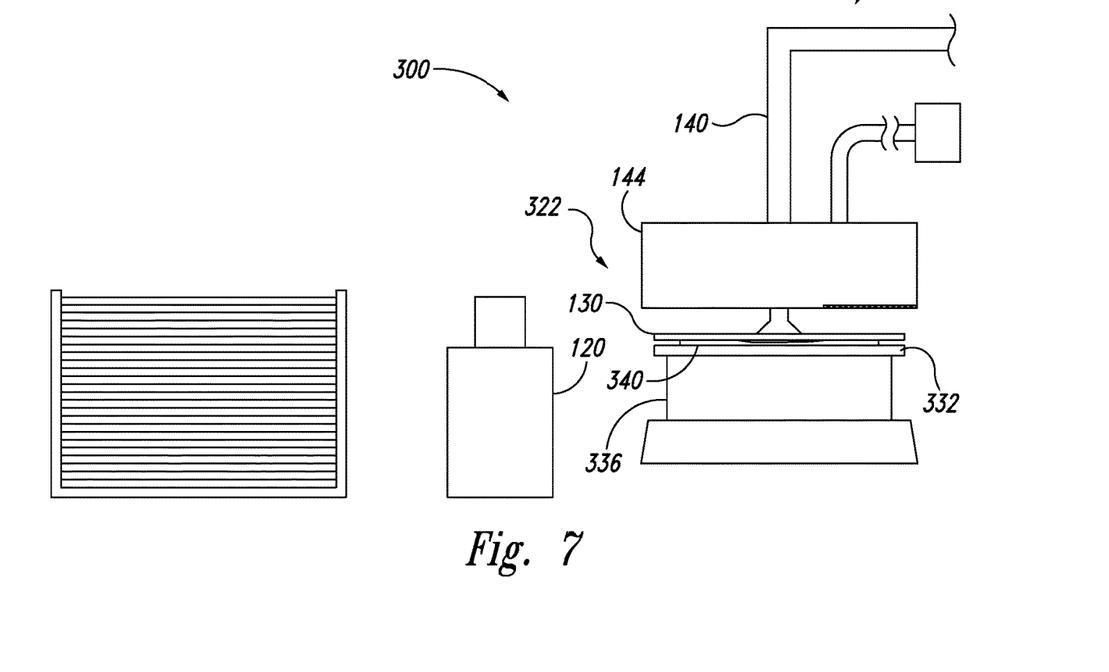
FIG. 7 is a front view of the coverslipper of FIG. 5 placing a coverslip on a specimen-bearing slide in accordance with one embodiment.

FIG. 5 is a front view of a coverslipper 300 ready to pick up a coverslip 130 in accordance with one embodiment. FIG. 6 is a front view of the coverslipper 300 ready to detect the number of coverslips carried by the holder mechanism 144. FIG. 7 is a front view of the coverslipper 300 placing the coverslip 130 on a specimen-bearing slide 332. Referring to FIG. 5, the coverslipper 300 can include a coverslip loading or pickup station 310 ("loading station 310"), a detection station 320, and a mounting station 322. The loading station 310 can include a carrier 330 (e.g., a cassette, a cartridge, a magazine, etc.) holding coverslips 130 stacked in a substantially vertical arrangement but can include other types of carriers (e.g., trays that carry coverslips in a horizontal arrangement).

The coverslips 130 can be generally circular shaped, rectangular shaped, square shaped, or any other suitable shape. In some embodiments, the coverslips are circular with diameters of 18 mm, 22 mm, or 25 mm. Square coverslips 130 can have sides with lengths of about 18 mm, 22 mm, or 25 mm. Rectangular coverslips 130 can have sides with lengths from about 11 mm×22 mm to about 48 mm×60 mm. The dimensions, shapes, and properties of the coverslips can be selected based on, for example, the size of the microscope slides. The coverslips 130 can be made, in whole or in part, of transparent plastic, glass, or other transparent or semi-transparent materials. In some embodiments, bottom surfaces of coverslips (e.g., glass plate coverslips) are coated with an adhesive, such as an activatable adhesive. The activatable adhesives can be, for example, dry activatable toluene, xylene, or the like.

FIG. 5 shows the holder mechanism 144 positioned at a loading or pickup position 307. The pickup head 154 is at a lowered or deployed position to contact or be close to the upper surface 181 of the uppermost coverslip 130 such that a vacuum can be drawn to hold the upper surface 181 against the head 154. After the holder mechanism 144 holds the coverslip 130, the transport mechanism 140 can lift the coverslip 130 from the stack 301. Additionally or alternatively, a reciprocally moveable plunger 312 can move through a bottom portion 313 of the carrier 330 to push the uppermost coverslip 130 into contact with the head 154. The plunger 312 can also be lowered to separate the stack 301 from the coverslip 130 retained by the pickup head 154.

The transport mechanism 140 can move the holder mechanism 144 from the loading station 310 to the detection station 320. FIG. 6 shows the holder mechanism 144 at a detection position such that the coverslip 130 is located at the detection zone 163. The front surface 211 of the coverslip 130 can be generally perpendicular to the light path 214 such that light reflected by the surface 211 travels back towards the sensor 120. For example, the angle of incidence can be equal to or less than about 5 degrees. Other angles of incidence are also possible.

After determining the holder mechanism 144 is holding only one coverslip, the holder mechanism 144 can carry the coverslip 130 to the mounting station 322. If the detection station 320 determines that the transport apparatus 110 is carrying multiple coverslips (e.g., a stack of coverslips stuck together), the transport apparatus 110 can deliver the coverslips to a rejected coverslip collection station. The rejected coverslip collection station can include one or more receptacles, cassettes, magazines, and can be periodically emptied or discarded.

FIG. 7 shows the coverslip 130 covering a specimen 340. The mounting station 322 can include, without limitation, a platform 336 configured to support the slide 332. The specimen 340 can be a biological specimen that includes one or more biological samples, which can be a tissue sample removed from a subject. The tissue sample can be a collection of cells, such as interconnected cells that perform a similar function within an organism. A biological sample can also be any solid or fluid sample obtained from, excreted by, or secreted by any living organism, including, without limitation, single-celled organisms, such as bacteria, yeast, protozoans, and amebas, multicellular organisms (e.g., plants or animals, including samples from a healthy or apparently healthy human subject or a human patient affected by a condition or disease to be diagnosed or investigated, such as cancer). In some embodiments, a biological sample includes, without limitation, a section of tissue, an organ, a tumor section, a smear, a frozen section, a cytology prep, or cell lines. An incisional biopsy, a core biopsy, an excisional biopsy, a needle aspiration biopsy, a core needle biopsy, a stereotactic biopsy, an open biopsy, or a surgical biopsy can be used to obtain the sample.

The slide 332 can be a 1 inch×3 inch microscope slide, a 25 mm×75 mm microscope slide, or another type of flat or substantially flat substrate. "Substantially flat substrate" refers, without limitation, to any object having at least one substantially flat surface, but more typically to any object having two substantially flat surfaces on opposite sides of the object, and even more typically to any object having opposed substantially flat surfaces, which opposed surfaces are generally equal in size but larger than any other surfaces on the object. In some embodiments, the substantially flat substrate can comprise any suitable material, including plastics, rubber, ceramics, glass, silicon, semiconductor materials, metals, combinations thereof, or the like. Non-limiting examples of substantially flat substrates include SELDI and MALDI chips, silicon wafers, or other generally planar objects with at least one substantially flat surface.

Referring to FIGS. 5-7, the coverslipper 300 can be an automated coverslipper. Coverslips and/or specimen-bearing slides can be manually loaded into the coverslipper 300, which can sequentially cover each specimen-bearing microscope slide with a single coverslip. The coverslipped microscope slides can be removed from the coverslipper 300 for analysis and/or storage.

Figure 8:
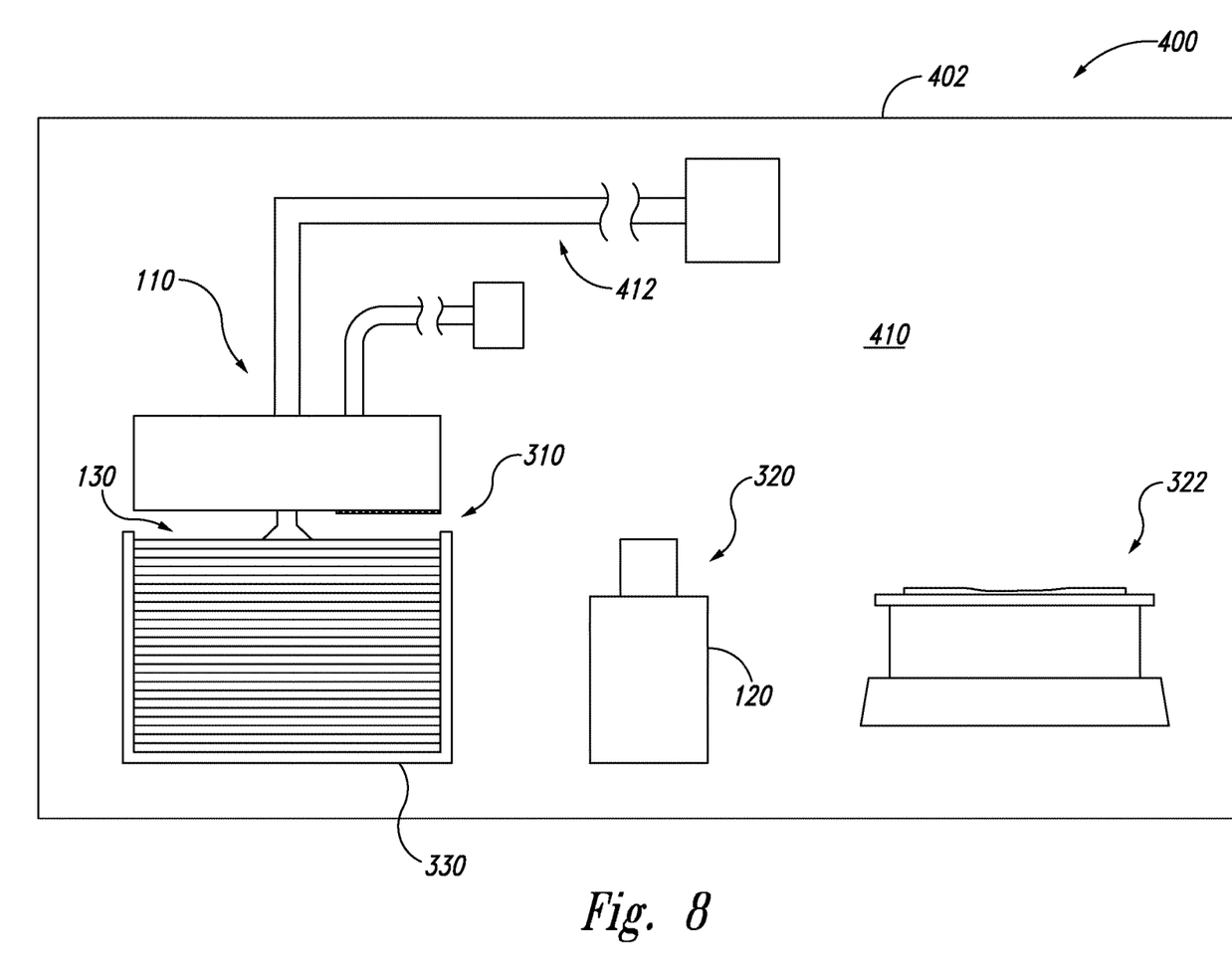
FIG. 8 is a front view of a coverslipper in accordance with another embodiment.

FIG. 8 shows a portable coverslipper 400 that can be readily carried by a person. In a laboratory setting, the coverslipper 400 can be manually transported between workstations and can include a protective housing 402 for inhibiting, limiting, or substantially preventing contaminants from entering an internal chamber 410. The protective housing 402 can include, without limitation, a cover or a door that can be opened to access internal components, including, without limitation, transport apparatus 412 (e.g., conveyors, actuators, etc.), robotic components (e.g., robotic arms), slide holding stations, or the like. For example, the cover can be opened to manually place a coverslip carrier 330 (illustrated loaded with a stack of coverslips) into the loading station 310.

Figure 9:
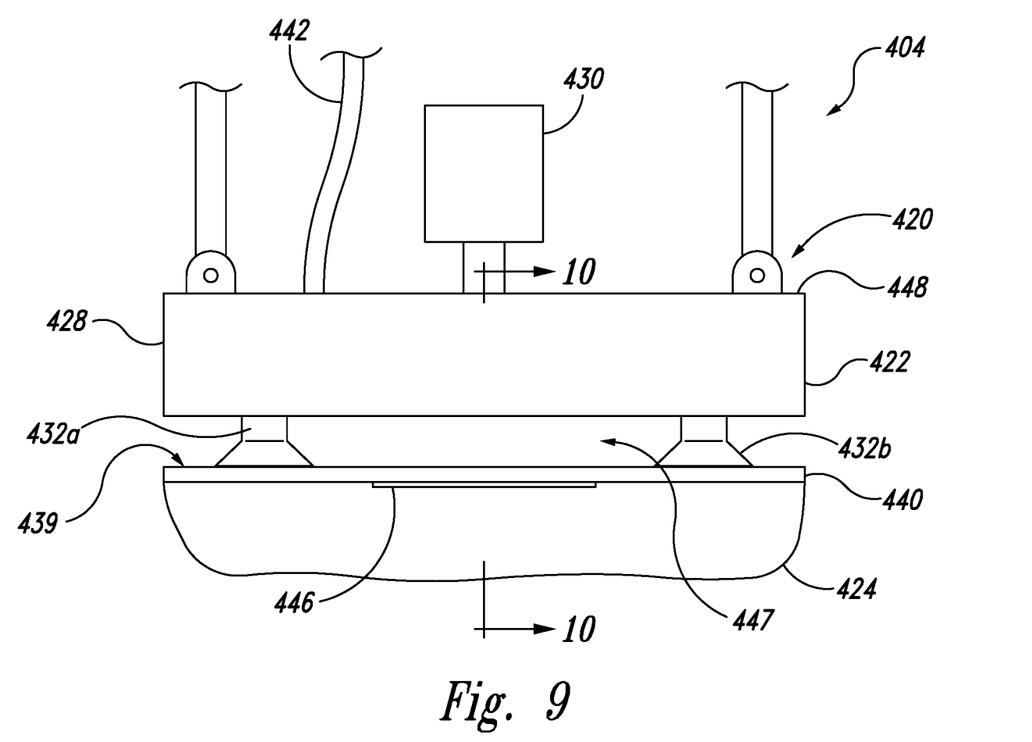
FIG. 9 is a front view of a coverslip detector in accordance with another embodiment.

FIG. 9 is a front view of a coverslip detector 404 that is generally similar to the coverslip detector 100 discussed in connection with FIGS. 1-7, except as detailed below. The coverslip detector 404 can include a coverslip holder mechanism 422 and a backing element 424. The coverslip holder mechanism 422 can include a main body 428, a sensor 430, and pickup heads 432a, 432b (collectively "pickup heads 432"). A vacuum can be drawn between the heads 432 and a coverslip 440 via a line 442. The backing element 424 can include an optical element 446 (e.g., a noise reducing element, an optically anti-reflective element, etc.) to enhance performance of the sensor 430. A detection zone 447 is defined between the coverslip holder mechanism 422 and the optical element 446. In some embodiments, the sensor 430 can be mounted on a backside of the main body 428. In other embodiments, the sensor 430 can be embedded in the main body 428 or located at another position.

Figure 10:
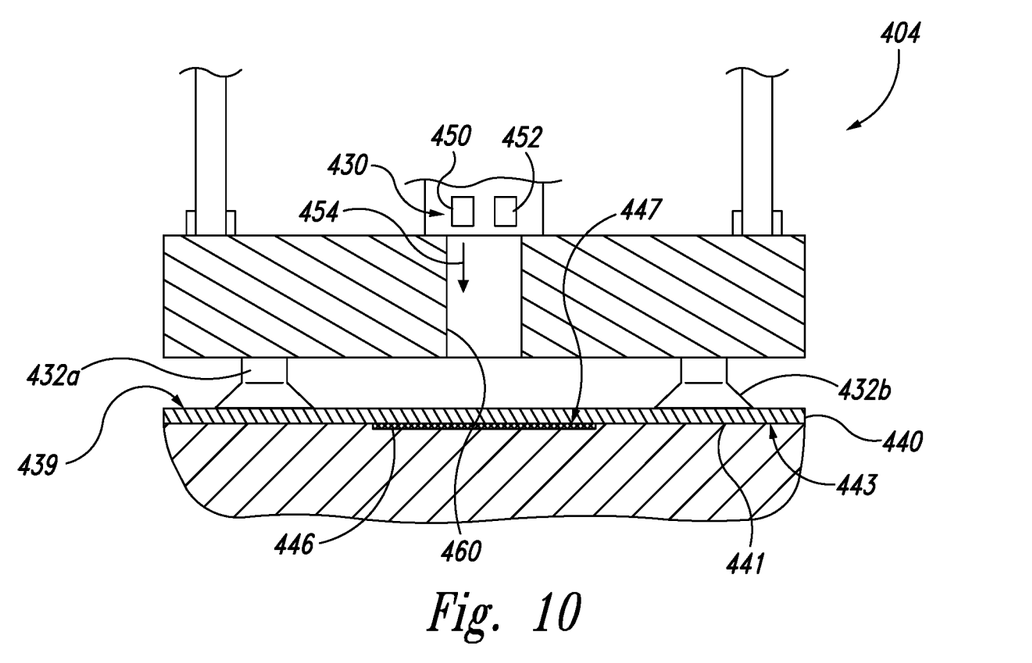
FIG. 10 is a cross-sectional view of the coverslip detector taken along line 10-10 of FIG. 9.

FIG. 10 is a cross-sectional view of the coverslip detector 404 along line 10-10 of FIG. 9. The sensor 430 includes a light source 450 that can produce light (represented by arrow 454) that travels through an opening 460 (e.g., a through hole, an aperture, etc.) in the main body 428. For example, the diameter of the opening 460 can be decreased or increased to decrease or increase scattering of light. A portion of the light 454 can be reflected by a front surface 439 of the coverslip 440 and detected (e.g., identified, measured, analyzed, etc.) by a light detector 452. The optical element 446 can be positioned on the backside 441 of the coverslip 440 to inhibit, limit, or to substantially eliminate noise attributable of reflection by the backing element 424. In some embodiments, the coverslip 440 lays generally flat on the backing element 424 such that the backside surface 443 contacts an upper surface 447 of the optical element 446.

Figure 11A:
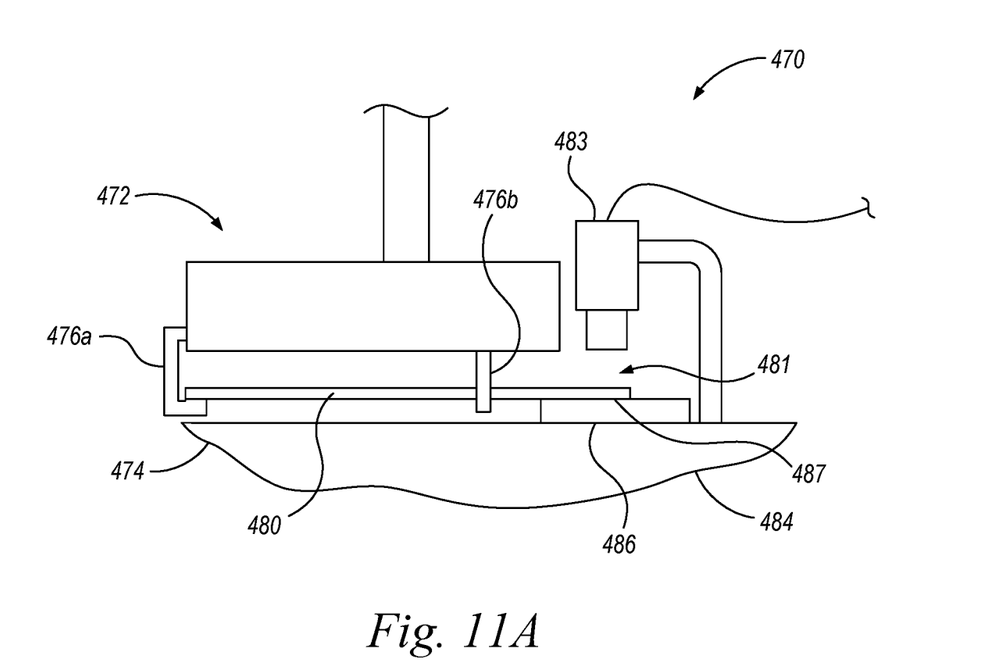
FIGS. 11A-C are front views of coverslip detectors in accordance with additional embodiments.
Figure 11B:
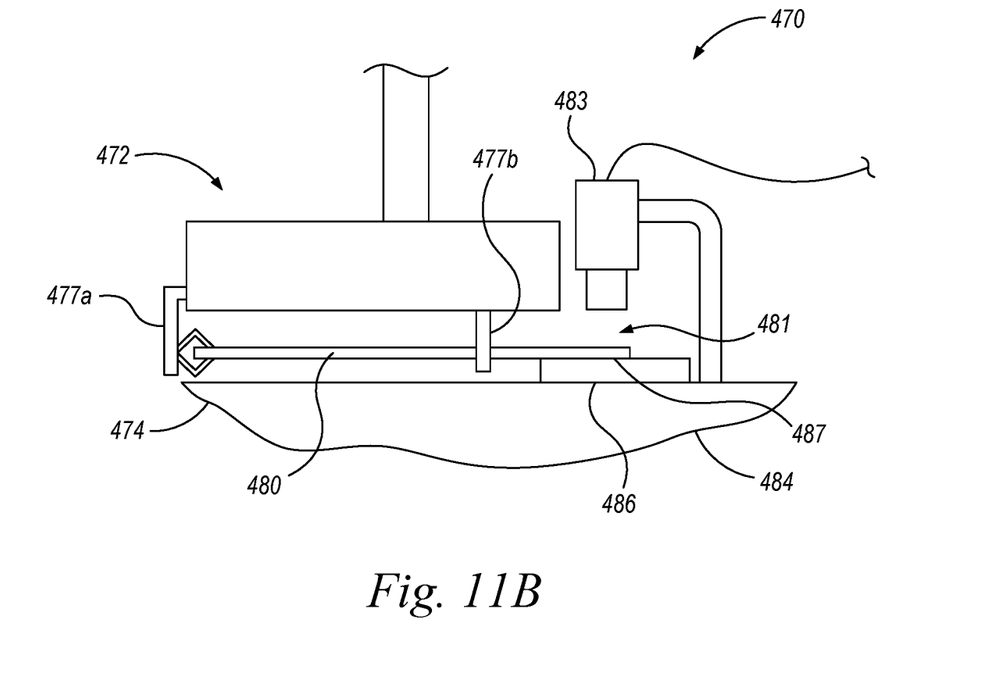
Figure 11C:
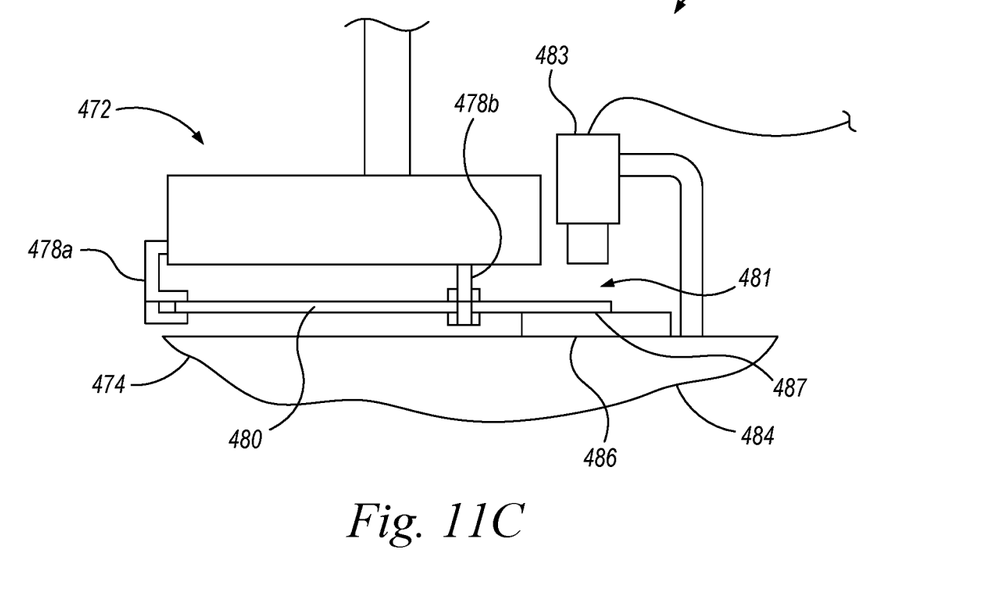

FIG. 11A is a front view of a stationary coverslip detector 470 in accordance with another embodiment. The coverslip detector 470 can be generally similar to the detectors discussed in connection with FIGS. 1-10, except as detailed below. The coverslip detector 470 can include a coverslip holder mechanism 472 ("holder mechanism 472") and a backing element 474. The holder mechanism 472 can mechanically hold and release coverslips using arms 476a, 476b (collectively "arms 476"). In other embodiments the mechanical holder mechanism 472 can include one or more pins, lifters, pinchers (e.g., pinchers 477a, 477b of FIG. 11B), clamps (e.g., clamps 478a, 478b of FIG. 11C), or the like.

The holder mechanism 472 can transport the coverslip 440 from a loading station to a detection zone 481. Advantageously, the stationary coverslip detector 470 can analyze coverslips carried by different types of holder mechanisms. The coverslip detector 470 can include a sensor 483 mounted to a backing element 484, which includes an optical element 486. After a portion 487 of the coverslip 480 is positioned within the detection zone 481, the sensor 483 can determine the number of coverslips.

Figure 12:
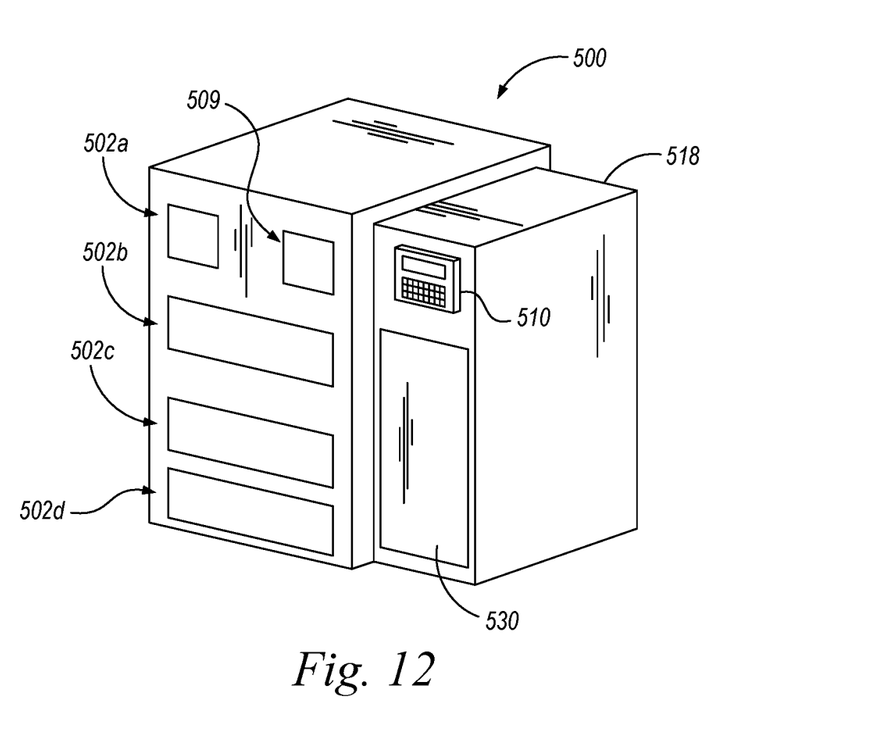
FIG. 12 is an isometric view of an automated slide processing apparatus in accordance with one embodiment.

FIG. 12 is an isometric view of an automated slide processing apparatus 500 ("apparatus 500") that includes processing stations 502a, 502b, 502c, 502d (collectively "processing stations 502") and a coverslipper station 509. The apparatus 500 can process wet microscope slides carrying freshly cut tissue specimens. An access door 530 can be opened, and a user can load specimen-bearing slides and coverslips into a transport device 518. The transport device 518 can sequentially deliver the microscope slides to the processing stations 502 to automatically process (e.g., via a process that is substantially free of human intervention) slides. As used herein, the term "processing station" includes, without limitation, a baking station, a material removal station (e.g., a de-waxing station, a de-paraffinizing station, or the like), staining station, or the like. For example, the processing stations 502a, 502b, 502c, 502d can be a baking station, a de-paraffinizing station, a staining station, and a baking/heating station, respectively. The number, location, and types of processing stations can be selected to provide the desired processing capability. The transport device 518 can deliver coverslips to the coverslipper station 509, which can include, without limitation, one or more coverslippers (e.g., coverslipper 300 or 400 of FIGS. 5-8), and the coverslipped slides can be removed using the access door 530.

A controller 510 can be communicatively coupled to and command the transport device 518, one or more of the processing stations 502, and the coverslipper station 509. The controller 510 can generally include, without limitation, one or more computers, central processing units, processing devices, microprocessors, digital signal processors (DSPs), application-specific integrated circuits (ASICs), readers, and the like. To store information (e.g., executable instructions), the controller 510 can include, without limitation, one or more storage elements, such as computer readable media, volatile memory, non-volatile memory, read-only memory (ROM), random access memory (RAM), or the like. The controller 510 can include one or more processors that are programmed with a series of computer-executable instructions that are stored on a non-transitory, computer readable media. The stored computer-executable instructions can include detection programs, calibration programs, tissue preparation programs, or other executable programs. Detection programs can be executed to detect coverslips using coverslip detectors of the coverslipper station 509. The detection program can include, for example, data for coverslips (e.g., optical characteristics) and can compare the stored data to the signal from the coverslip detector. Based on the comparison, the controller 510 can determine the number of coverslips. Optimization programs can be executed to optimize performance (e.g., increase productivity, enhance processing consistency, or the like). The processing may be optimized by determining, for example, an optimum schedule to (1) increase processing speeds, (2) reduce the coverslipping time, and/or (3) increase throughput (e.g., increase the number of slides processed in a certain length of time). The tissue preparation programs can be executed to perform tissue preparation protocols.

The transport device 518 can include, without limitation, one or more elevators, slide handlers, slide trays, slide holders, or the like. Slide handlers can include, but are not limited to, slide manipulators, X-Y-Z transport systems, robotic systems, or other automated systems capable of receiving and transporting slides and/or coverslips. A robotic system can include, without limitation, one or more pick and place robots, robotic arms, or the like.

Figure 13:
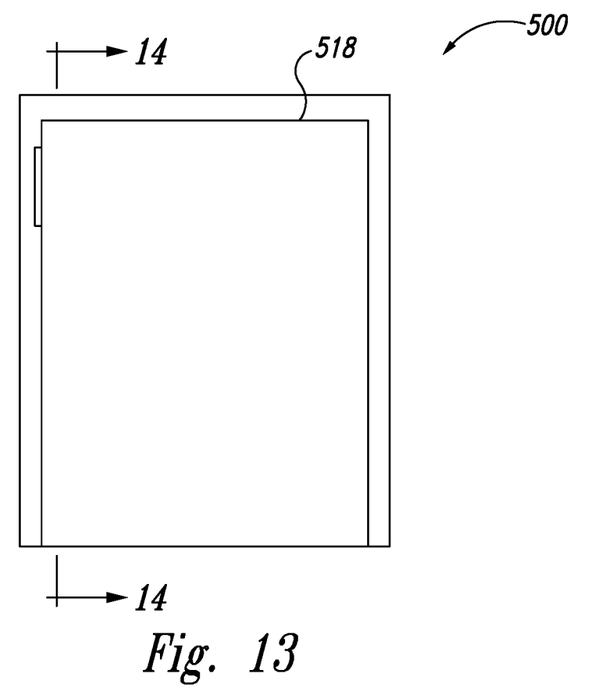
FIG. 13 is a side view of the automated slide processing apparatus of FIG. 12.
Figure 14:
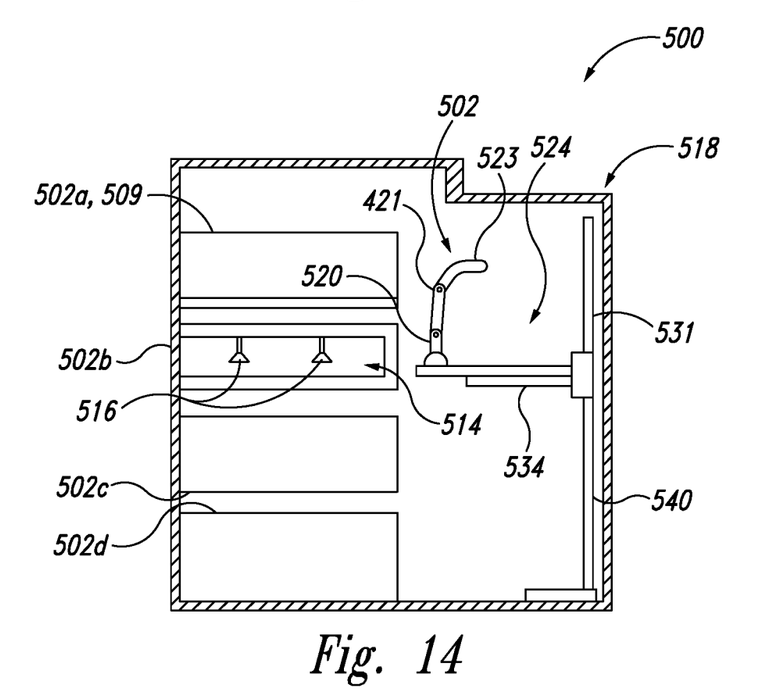
FIG. 14 is a cross-sectional view of the automated slide processing apparatus taken along line 14-14 of FIG. 13.

FIG. 14 is a cross-sectional view of the apparatus 500 along line 14-14 of FIG. 13. The transport device 518 can include a transporter 524, an elevator system 531, and a movable platform 534. The elevator system 531 moves the transporter 524 up and down along a rail 540. A slide handler 520, illustrated as a robotic slide handler, can transport slides between the stations 502 and coverslipper station 509. The illustrated transport device 518 is positioned to load the slides into the processing station 502a.

Specimen-carrying microscope slides can be loaded onto a slide tray, which is placed on the platform 534. The slide handler 520 can load the specimen-carrying microscope slides into the processing station 502a. The processing station 502a can dry the specimen-carrying microscope slides. After the specimen-carrying microscope slides are dried a sufficient amount, the slide transporter 524 can transport the slides back to the tray. The transporter 542 can be vertically lowered and positioned adjacent to the processing station 502*b* for de-paraffinizing.

The de-paraffinizing station 502*b* is capable of removing at least a portion of the embedding material of the specimen. The de-paraffinizing station 502*b* can be a bath-type, de-paraffinizing station or a spray-type, de-paraffinizing station. The illustrated de-paraffinizing station 502*b* includes a modular compartment 514 and includes one or more wash dispense nozzles 516 directed downwardly. De-paraffinizing substances are delivered onto the specimens using the nozzles 516. After removing the embedding material (e.g., paraffin), the slides can be rinsed with substances, such as de-ionized water, to remove the de-paraffinizing substance and the extra paraffin leaving the bare tissue sample adhered to the microscope slide. The de-paraffinizing substances can be fluids, for example, aqueous-based fluids that promote separation of paraffin and tissue specimens, such as those disclosed in U.S. Pat. No. 6,855,559, issued Feb. 15, 2005 and U.S. Pat. No. 6,544,798, issued Apr. 8, 2003, including de-ionized water, citrate buffer (pH 6.0-8.0), tris-HCl buffer (pH 6-10), phosphate buffer (pH 6.0-8.0), acidic buffers or solutions (pH 1-6.9), basic buffers or solutions (pH 7.1-14), or the like. The substance may also contain one or more ionic or non-ionic surfactants. The de-paraffinizing substances can be heated. For example, the substances (e.g., fluids) may be heated to a temperature greater than the melting point of the embedding material, e.g., between 60-70 degrees Celsius. U.S. Pat. No. 7,303,725, issued Dec. 4, 2007, discloses various components (e.g., probes, filters, sprayers, etc.) for use with de-paraffinizing substances. In some embodiments, the station 502*b* also includes one or more heating elements for baking the embedding material. The slides can be heated to soften the embedding material to facilitate material removal.

After the station 502*b* has processed the specimen-carrying slides, the transporter 524 can deliver the specimen-carrying slides to the station 502*c* for staining. A desired stain is applied by the staining station 502*c* to the tissue samples. The stain can be a biological or chemical substance which, when applied to targeted molecules in tissue, renders the tissue detectable under an instrument. Stains include, without limitation, detectable nucleic acid probes, antibodies, hematoxylin, eosin, and dyes (e.g., iodine, methylene blue, Wright's stain, etc.). For example, immunohistochemical and in situ hybridization staining processes can be performed on the specimens.

After the specimens are stained, the specimen-bearing slides are transported to the station 502*d* capable of draining excess liquids (e.g., solvents) from the slides. After draining, the specimen-bearing slides are transported to the coverslipping station 509, which can be similar or identical to the coverslipper 300 of FIGS. 5-7 or the coverslipper 400 of FIG. 8. After the coverslipping station 509 coverslips the slides, the coverslipped slides can be subsequently removed from the apparatus 500.

The embodiments disclosed herein can also have other features for inhibiting or preventing light from returning back to the detectors. In some embodiments, a reflective surface can be positioned behind the surface of the coverslip opposite the optical sensor. The reflective surface can reflect light that travels through the coverslip(s) away from the optical sensor. For example, the anti-reflective element 160 of FIG. 1 can be a mirror or a reflective surface oriented to reflect light away from the detector 178 (FIG. 3). Other types of components can also be used to block or otherwise prevent light from returning back to the optical sensor.

The detectors disclosed herein can be used to analyze different types of items. Such items can include, without limitation, semi-transparent substrates, transparent substrates, or other items capable of reflecting light. For example, the detector 100 can detect substrates in the form of transparent sheets (e.g., screens for computers, screens for tablets, screens for smartphones, screens for touch screen devices, screens for televisions, etc.), watch glasses or crystals, or the like. In some embodiments, the detectors disclosed herein can be incorporated to manufacturing or production lines that assemble electronic devices (e.g., computers, tablets, smartphones, etc.), watches, or other devices with substrates.

From the foregoing, it will be appreciated that specific embodiments of the invention have been described herein for purposes of illustration, but well-known structures and functions have not been shown or described in detail to avoid unnecessarily obscuring the description of at least some embodiments of the invention. Where the context permits, singular or plural terms may also include the plural or singular term, respectively. Unless the word "or" is associated with an express clause indicating that the word should be limited to mean only a single item exclusive from the other items in reference to a list of two or more items, then the use of "or" in such a list shall be interpreted as including (a) any single item in the list, (b) all of the items in the list, or (c) any combination of the items in the list. The singular forms "a," "an," and "the" include plural referents unless the context clearly indicates otherwise. Thus, for example, reference to "a sensor" refers to one or more sensors, such as two or more sensors, three or more sensors, or four or more sensors. This application is related of U.S. application Ser. No. 13/786,356, filed Mar. 5, 2013, which is hereby incorporated by reference in its entirety.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An automated microscope processing apparatus, comprising:
a processing station configured to robotically apply liquid to specimen-bearing microscope slides, wherein the processing station has one or more nozzles configured to robotically apply the liquid onto the specimen-bearing microscope slides; and
a coverslip detector including
a coverslip holder mechanism for holding a coverslip, wherein the coverslip holder mechanism is selected from a group consisting of a coverslip holder vacuum mechanism and a coverslip holder mechanical mechanism,
an anti-reflective optical element positioned along the coverslip holder mechanism,
a reflectance sensor including a light source configured to output light towards the anti-reflective optical element and a light detector configured to detect the outputted light, which has been reflected by any coverslips carried by the coverslip holder mechanism, and
a controller communicatively coupled to the reflectance sensor and programmed to determine whether the coverslip holder mechanism is carrying more than one coverslip based on one or more signals from the reflectance sensor indicative of the detected light.

2. The coverslip detector of claim 1, further comprising a transport mechanism configured to robotically move the coverslip holder mechanism from a coverslip pick up position to a coverslip detection position, wherein the transport mechanism includes at least one of a robotic arm, a conveyor, a rail assembly, or combinations thereof, wherein the controller is programmed to command the coverslip detector to transport individual coverslips held by the transport mechanism to the processing station.

3. A coverslip detector for detecting microscope slide coverslips, the coverslip detector comprising:
 a coverslip holder mechanism for holding a microscope slide coverslip, the coverslip holder mechanism is a coverslip holder vacuum mechanism or a coverslip holder mechanical mechanism,
 an anti-reflective optical element positioned along the coverslip holder mechanism;
 a reflectance sensor including a light source configured to output light towards the anti-reflective optical element, the reflectance sensor including a light detector configured to detect the outputted light that has been reflected by any microscope slide coverslips carried by the coverslip holder mechanism and positioned between the reflectance sensor and the anti-reflective optical element; and
 a controller communicatively coupled to the reflectance sensor and including one or more processors and non-transitory, computer readable media with instructions, executable by the one or more processors, to determine if the coverslip holder mechanism is carrying more than one microscope slide coverslip based on one or more signals from the reflectance sensor indicative of the detected light.

4. The coverslip detector of claim 3, wherein the anti-reflective optical element is positioned along an optical path along which the outputted light travels toward the anti-reflective optical element when the coverslip holder mechanism is at the coverslip detection position.

5. The coverslip detector of claim 3, wherein when the one or more processors execute the instructions, the controller compares data stored by the non-transitory, computer readable media and data from the reflectance sensor to determine if the coverslip holder mechanism is carrying more than one coverslip.

6. The coverslip detector of claim 3, wherein when the one or more processors execute the instructions, the controller correlates the detected light to at least one of
 a microscope slide coverslip absence,
 a presence of at least one microscope slide coverslip between the reflectance sensor and the anti-reflective optical element, or
 a number of microscope slide coverslips between the reflectance sensor and the anti-reflective optical element.

7. The coverslip detector of claim 3, wherein when the one or more processors execute the instructions, the controller further determines if the coverslip holder mechanism is carrying a single microscope slide coverslip based on measured reflected light intensity and a stored reference light intensity.

8. The coverslip detector of claim 3, wherein the anti-reflective optical element absorbs outputted light that has passed through the microscope slide coverslip.

9. The coverslip detector of claim 3, wherein the anti-reflective optical element inhibits optical noise with the light from the reflectance sensor that is reflected by the one or more coverslips carried by the coverslip holder mechanism.

10. The coverslip detector of claim 3, wherein the coverslip holder mechanism is positionable to hold the microscope slide coverslip along an optical path from the reflectance sensor to the anti-reflective optical element.

11. The coverslip detector of claim 3, wherein the anti-reflective optical element includes a black surface, a black coating, and/or a black film.

12. The coverslip detector of claim 3, wherein the anti-reflective optical element absorbs incident light from the reflectance sensor such that an amount of light, if any, reflected by the coverslip holder mechanism and the anti-reflective optical element is less than an amount of light reflected by a single microscope slide coverslip.

13. The coverslip detector of claim 3, wherein the anti-reflective optical element absorbs most of the light from the reflectance sensor that strikes the optically anti-reflective optical element.

14. The coverslip detector of claim 3, wherein the anti-reflective optical element prevents reflection of at least a portion of incident light from the reflectance sensor to enable the reflectance sensor to detect a number of microscope slide coverslips carried by the coverslip holder mechanism.

15. A coverslip detector for detecting microscope slide coverslips, the coverslip detector comprising:
 a coverslip holder mechanism for holding a microscope slide coverslip, wherein the coverslip holder mechanism is a coverslip holder vacuum mechanism or a coverslip holder mechanical mechanism;
 an anti-reflective optical element positioned along the coverslip holder mechanism;
 a photoelectric sensor that outputs light toward the anti-reflective optical element, the photoelectric sensor is positioned to detect the outputted light that has been reflected by each microscope slide coverslip carried by the coverslip holder mechanism; and
 a controller communicatively coupled to the photoelectric sensor and including one or more processors and non-transitory, computer readable memory with programming for determining if the coverslip holder mechanism is holding more than one microscope slide coverslip based on the detection of the reflected light.

16. The coverslip detector of claim 15, wherein the controller determines if the coverslip holder mechanism is carrying multiple microscope slide coverslips based on the detection of the reflected light.

17. The coverslip detector of claim 15, wherein the detection of the reflected light includes measuring reflected light intensity.

18. The coverslip detector of claim 15, wherein the anti-reflective optical element has a reflectivity less than about 0.1 for the one or more wavelengths emitted by the reflectance sensor.

19. The coverslip detector of claim 15, wherein the optically anti-reflective element includes a light-absorbing, low-remission surface that is less optically reflective than glass.

20. The coverslip detector of claim 15, wherein the reflectance sensor is configured to detect the light reflected by one or more coverslips positioned within a coverslip detection zone while light from the reflectance sensor, which is transmitted through the one or more coverslips, strikes the anti-reflective optical element.

21. The coverslip detector of claim 20, further comprising a coverslip transport apparatus configured to move the coverslip holder mechanism into and out of the coverslip detection zone, wherein the coverslip transport apparatus includes at least one of a robotic arm, a conveyor, a rail assembly, a motor, or combinations thereof.

22. The coverslip detector of claim 15, wherein the reflectance sensor is spaced apart from the coverslip holder mechanism when the coverslip holder mechanism is at a coverslip detection position such that the coverslip holder mechanism is capable of holding two or more coverslips spaced apart from the reflectance sensor.

23. The coverslip detector of claim 15, wherein the anti-reflective optical element is a low-remission surface of the coverslip holder mechanism.

24. The coverslip detector of claim 15, wherein the controller is in communication with a transport apparatus operable to move the coverslip holder mechanism to sequentially retrieve microscope slide coverslips and place the retrieved microscope slide coverslip on respective microscope slides.

25. The coverslip detector of claim 15, wherein the controller is programmed to determine a number of the coverslips in a coverslip detection zone based, at least in part, on the detected light.

26. The coverslip detector of claim 3, wherein the coverslip holder mechanism is the coverslip holder mechanical mechanism, which includes a plurality of pinchers and/or clamps.

* * * * *